(12) United States Patent
Kim

(10) Patent No.: US 11,406,301 B2
(45) Date of Patent: Aug. 9, 2022

(54) SYSTEM AND METHOD FOR DETECTING EMOTIONAL STATE OF PET

(71) Applicant: PETPULS LAB INC., Anyang-si (KR)

(72) Inventor: Cheongyeup Kim, Anyang-si (KR)

(73) Assignee: PETPULS LAB INC., Anyang-si (KR)

( * ) Notice: Subject to any disclaimer, the term of this patent is extended or adjusted under 35 U.S.C. 154(b) by 0 days.

(21) Appl. No.: 17/270,715

(22) PCT Filed: Apr. 30, 2019

(86) PCT No.: PCT/KR2019/005198
§ 371 (c)(1),
(2) Date: Feb. 23, 2021

(87) PCT Pub. No.: WO2020/045789
PCT Pub. Date: Mar. 5, 2020

(65) Prior Publication Data
US 2022/0000404 A1 Jan. 6, 2022

(30) Foreign Application Priority Data
Aug. 30, 2018 (KR) .......................... 10-2018-0102429

(51) Int. Cl.
*A61B 5/16* (2006.01)
*A01K 29/00* (2006.01)
(Continued)

(52) U.S. Cl.
CPC ............ *A61B 5/165* (2013.01); *A01K 29/005* (2013.01); *A61B 5/01* (2013.01); *A61B 5/11* (2013.01);
(Continued)

(58) Field of Classification Search
CPC .. A61B 5/165; A61B 5/01; A61B 5/11; A61B 5/7275; A61B 2562/06; A61B 5/00;
(Continued)

(56) References Cited

U.S. PATENT DOCUMENTS

2003/0166996 A1* 9/2003 Kim ...................... A61B 5/165
600/300
2006/0258914 A1* 11/2006 Derchak ............... A61B 5/6805
600/300
(Continued)

FOREIGN PATENT DOCUMENTS

KR 10-2011-0011768 A 2/2011
KR 10-2016-0081468 A 7/2016
(Continued)

OTHER PUBLICATIONS

International Search Report for PCT/KR2019/005198 dated Aug. 9, 2019 from Korean Intellectual Property Office.

*Primary Examiner* — Ryan W Sherwin
(74) *Attorney, Agent, or Firm* — Paratus Law Group, PLLC

(57) ABSTRACT

Disclosed is a system for detecting an emotional state of a companion animal, including: a state information collecting device comprising a microphone and sound sensor which collects a sound of the companion animal, a temperature sensor which collects a temperature of the companion animal, and an acceleration sensor which collects an activity of the companion animal, the state information collecting device being worn on a body of the companion animal; and a companion-animal emotion analysis server configured to extract characteristic information of sound information of the companion animal transmitted from the state information collecting device, select emotional state information of the companion animal corresponding to the extracted characteristic information from a database, and transmit the selected emotional state information of the companion animal through a wireless communication network to a portable terminal of an animal guardian.

5 Claims, 7 Drawing Sheets

(51) Int. Cl.
*A61B 5/01* (2006.01)
*A61B 5/11* (2006.01)
*A61B 5/00* (2006.01)

(52) U.S. Cl.
CPC ........ *A61B 5/7275* (2013.01); *A61B 2562/06* (2013.01)

(58) Field of Classification Search
CPC . A61B 5/16; A61B 5/0024; A61B 2562/0219; A01K 29/005
See application file for complete search history.

(56) References Cited

U.S. PATENT DOCUMENTS

| | | | | |
|---|---|---|---|---|
| 2008/0236514 | A1* | 10/2008 | Johnson | A01K 15/021 119/719 |
| 2016/0015004 | A1* | 1/2016 | Bonge, Jr. | G01S 19/16 119/718 |
| 2016/0057395 | A1* | 2/2016 | Yuki | A01K 29/005 348/222.1 |
| 2016/0135431 | A1* | 5/2016 | Sheldon | H02J 13/00002 119/859 |
| 2016/0302393 | A1* | 10/2016 | Pradeep | A01K 29/005 |
| 2017/0064924 | A1* | 3/2017 | Stout | B05B 9/0426 |
| 2018/0055016 | A1* | 3/2018 | Hsieh | A01K 27/001 |
| 2018/0235182 | A1* | 8/2018 | Bocknek | A61B 5/6801 |
| 2019/0362727 | A1* | 11/2019 | Lee | A01K 29/005 |

FOREIGN PATENT DOCUMENTS

| | | |
|---|---|---|
| KR | 10-2017-0014208 A | 2/2017 |
| KR | 10-2018-0034143 A | 4/2018 |
| KR | 10-2018-0076468 A | 7/2018 |

* cited by examiner

SYSTEM AND METHOD FOR DETECTING EMOTIONAL STATE OF PET

CROSS-REFERENCE TO PRIOR APPLICATIONS

This application is a National Stage Patent Application of PCT International Patent Application No. PCT/KR2019/005198 (filed on Apr. 30, 2019) under 35 U.S.C. § 371, which claims priority to Korean Patent Application No. 10-2018-0102429 (filed on Aug. 30, 2018), which are all hereby incorporated by reference in their entirety.

BACKGROUND

The present disclosure relates to a method and device for detecting an emotional state of a companion animal and, more particularly, to a system and method for detecting an emotional state of a companion animal, in which a state information collecting device having a microphone, a temperature sensor, and an acceleration sensor capable of detecting the sound, temperature, and activity of the companion animal is worn on a portion of an animal body, information collected in the state information collecting device is analyzed, and then information about an emotional state of the companion animal is transmitted to a portable terminal possessed by an animal owner.

Not long ago, dogs and cats raised at home were called pets. However, these days, they are called companion animals. The companion animal is not an animal raised to give an owner pleasure or benefits, but means an animal which is respected as life and is a member of a family communing with people while living with them. In the modern society where a nuclear family and independent life are preferred, there is a tendency of performing emotional exchanges through animals, so that the number of people raising the companion animals is increasing. In Korea, it is known that the number of registered companion animals exceeds one million, and government policies to develop companion-animal industry are also being proposed.

There are many research results showing that companion animals play a positive role in improving the quality of human life. As for children, the companion animal helps develop sociability and emotion, encourages a sense of responsibility and mind of understanding others, promotes a language acquisition capability, and imprints the sanctity of life. Meanwhile, as for the elderly, the companion animal maintains good physical and mental health and increases positive thinking and life satisfaction.

Companion-animal experts often say that "modern people heal tired mind when they are betrayed by people, by raising companion animals which like and obey their owners", and "companion animals actually give people emotional stability". Indeed, companion animals are proven to be effective in preventing depression of people who live alone.

However, people's perception towards companion animals still remains within the boundary of pets.

For this reason, it is necessary to think about what to do and how to do for companion animals living together with people. To this end, it is necessary to first understand the emotional state of companion animals, as in people.

In order to satisfy the necessity, Korean Patent Publication No. 2016-0062800 has proposes "System and Method for Managing Pet using Pet-Suit". This accurately identifies the state of a pet by learning from a pet-suit which is worn on a pet to check pulse and temperature and then generate a sensing signal, and the sensing signal transmitted from the pet-suit, thus giving optimal environment to the pet.

The pet-suit proposed in the cited document includes a pulse sensor which checks the pulse of the pet to generate a pulse signal; a temperature sensor which checks the temperature of the pet to generate a temperature signal; a control unit which controls the transmission of the pulse signal and the temperature signal; and a communication unit which transmits the pulse signal and the temperature signal to a local server.

The conventional pet-suit is configured to measure only the pulse or the temperature and thereby check the state of the pet, but is problematic in that pets have various body sizes and may be thickly or thinly haired, so that it is difficult to accurately measure the pulse of pets.

SUMMARY

The present disclosure is to provide a system and method for detecting an emotional state of a companion animal, in which a sound generated by the companion animal, that is, sound characteristics can be analyzed and then the emotional state of the companion animal can be precisely transmitted to a portable terminal of a guardian in real time.

In order to solve the aforementioned problem, the present disclosure proposes a method for detecting an emotional state of a companion animal, the method including (a) wearing a state information collecting device on a body of the companion animal, the state information collecting device including a microphone into which a companion-animal sound is input, a temperature detection sensor which detects a temperature of the companion animal, and a three-axis acceleration sensor which detects an activity of the companion animal; (b) storing sound information in the state information collecting device during a predetermined time when the companion-animal sound is generated; (c) transmitting the sound information, temperature information, and activity information of the companion animal detected in the microphone, the temperature detection sensor, and the three-axis acceleration sensor to a companion-animal emotion analysis server through wireless communication; (d) deducing emotion information of the companion animal by gathering the sound information, the temperature information, and the activity information in the companion-animal emotion analysis server; and (e) transmitting information about the emotional state of the companion animal from the companion-animal emotion analysis server to a portable terminal of an animal guardian.

The present disclosure proposes a method for detecting an emotional state of a companion animal, the method including (a) wearing, on a portion of an animal body, a state information collecting device which receives state information of the companion animal; (b) selecting and inputting a kind of the companion animal through an input unit of the state information collecting device; (c) receiving a sound of the companion animal through a microphone that is a component of the state information collecting device, on the basis of a predetermined time; (d) transmitting kind information and sound information of the companion animal to a companion-animal emotion analysis server using a wireless communication network; (e) extracting characteristic information of the sound information; (f) selecting predetermined state information corresponding to the kind information and the characteristic information of the companion animal in a database; and (g) transmitting the state information to a portable terminal of an animal guardian using a wireless communication network, wherein the sound received through the microphone in (c) may be sampled in a predetermined sampling period in a time domain, and then be converted into a digital signal to be transmitted to the companion-animal emotion analysis server in (d), and the state information may be any one of various emotional states of the companion animal.

The extracting of the characteristic information in (e) may include extracting digital information of the sound using spectrogram information for time and frequency domains.

The present disclosure proposes a system for detecting an emotional state of a companion animal, the system including a state information collecting device including a microphone and sound sensor which collects a sound of the companion animal, a temperature sensor which collects a temperature of the companion animal, and an acceleration sensor which collects an activity of the companion animal, the state information collecting device being worn on a body of the companion animal; and a companion-animal emotion analysis server configured to extract characteristic information of sound information of the companion animal transmitted from the state information collecting device, select emotional state information of the companion animal corresponding to the extracted characteristic information from a database, and transmit the selected emotional state information of the companion animal through a wireless communication network to a portable terminal of an animal guardian.

The sound of the companion animal received through the microphone and sound sensor of the state information collecting device may be sampled in a predetermined sampling period in a time domain, and then be converted into a digital signal to be transmitted to the companion-animal emotion analysis server.

The companion-animal emotion analysis server may perform characteristic information extraction of digital information of the sound using spectrogram information for time and frequency domains.

Furthermore, the companion-animal emotion analysis server may select information about the emotional state of the companion animal from the database by combining at least one of temperature information and activity information of the companion animal collected by the temperature sensor and the acceleration sensor of the state information collecting device with the sound information.

A system and method for detecting an emotional state of a companion animal proposed in the present disclosure has the following effects.

First, the sound of the companion animal can be precisely analyzed, so that the emotional state of the companion animal can be transmitted in real time to a portable terminal possessed by an animal guardian.

Second, the emotional state of the companion animal can be more accurately identified by linking the analysis result of the frequency spectrum of sound which varies depending on the emotional state of the companion animal with the temperature information of the companion animal.

Third, an animal guardian can identify the emotional state of the companion animal in real time through his or her portable terminal at a close range or at a remote location, and can take certain measures.

DETAILED DESCRIPTION

Hereinafter, a system and method for detecting an emotional state of a companion animal in accordance with the present disclosure will be described with reference to the accompanying drawings.

Figure 1:
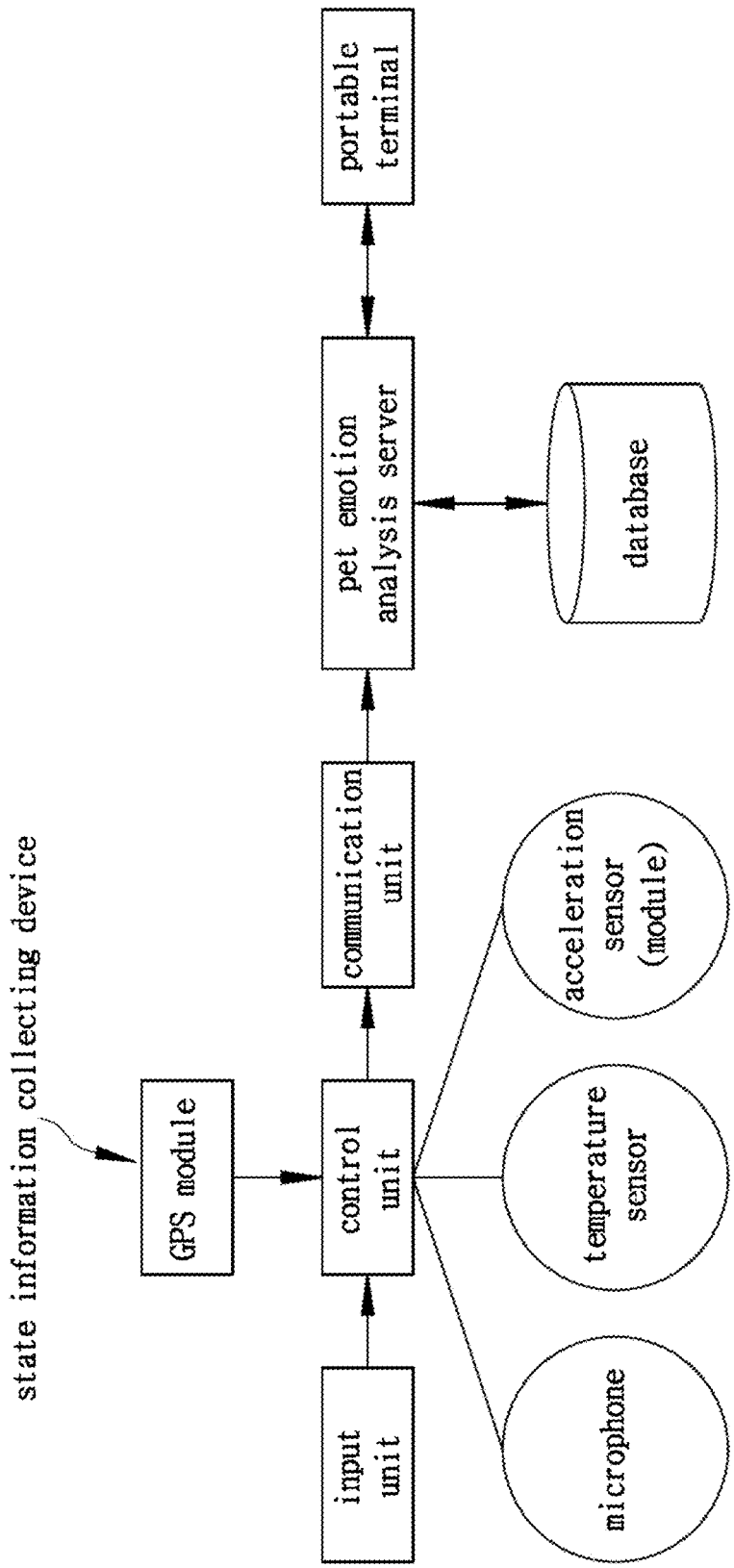
FIG. 1 is a conceptual view of an entire system for detecting an emotional state of a companion animal in accordance with the present disclosure.

FIG. 1 is a conceptual view of an entire system for detecting an emotional state of a companion animal in accordance with the present disclosure.

As illustrated in FIG. 1, the system for detecting the emotional state of the companion animal in accordance with the present disclosure includes a state information collecting device which is worn on a body of the companion animal, a companion-animal emotion analysis server which is linked wirelessly with the state information collecting device, a database in which learned information about emotion information of various pets is stored, and a portable terminal equipped with a predetermined application which may be linked wirelessly with the companion-animal emotion analysis server.

The state information collecting device of the present disclosure which is worn on the body of the companion animal to collect the emotional state information of the companion animal includes a microphone and sound sensor which collects the sound of the companion animal, a temperature sensor which collects the temperature of the companion animal, and an acceleration sensor which collects the activity of the companion animal. The state information collecting device may include a memory chip for storing collected information, a wireless communication module such as a WiFi communication module for transmitting information to the external pet emotion analysis server, and a battery supplying power to operate the sensor and the wireless communication module.

In order to implement the present disclosure, all the three types of sensors may be used, but a specific sensor may not be used if necessary.

For reference, the state information collecting device may further include a button or touch screen type of input unit, and may select the kind of the companion animal wearing the state information collecting device through an input unit.

In addition, the state information collecting device proposed in the present disclosure may be manufactured in the manner of being worn on the neck of the companion animal, and be implemented in the form of a harness. In other words, various types of devices which may correctly collect the sound, temperature, and activity of the companion animal may be further provided to implement the state information collecting device of the present disclosure in various ways.

Therefore, it is to be interpreted that the state information collecting device of the present disclosure embraces all types of devices which may be worn on the body of the companion animal to collect the sound, temperature, or activity of the companion animal.

For reference, the acceleration sensor of the present disclosure may comprise at least one acceleration sensor. For example, this may be installed on the neck of the companion animal, the ankle of the companion animal or the like. In other words, according to an embodiment of the present disclosure, in order to collect the activity of the companion animal from various aspects, the acceleration sensor may be installed on any part such as the neck of the companion animal, or the ankle or thigh of the companion animal.

For example, sensors may be attached to all the ankles of the companion animal so as to check the activity of the forefeet or hind legs of the companion animal. In this case, four acceleration sensors may be used.

In addition, in the case of adding the acceleration sensor to the neck of the dog, it is possible to collect the activity of the companion animal from various aspects through a total of five acceleration sensors.

For reference, when the activity of the companion animal is checked using at least one acceleration sensor, the state information collected from each acceleration sensor may be transmitted to the state information collecting device by wire, but may be wirelessly transmitted via short-range wireless communication.

For example, when the state information collecting device is implemented as a leash (neck band) device worn on the neck of the companion animal, four acceleration sensors worn on the ankle of the companion animal may be implemented as an acceleration sensor module which may perform wireless communication with the state information collecting device, namely, the leash device. In other words, in order to enable wireless communication with the leash, this may comprise four acceleration sensor modules each having a short-range wireless communication function. Therefore, the acceleration sensor of the present disclosure may receive information through various designs by selecting wire communication or short-range wireless communication.

Figure 2:
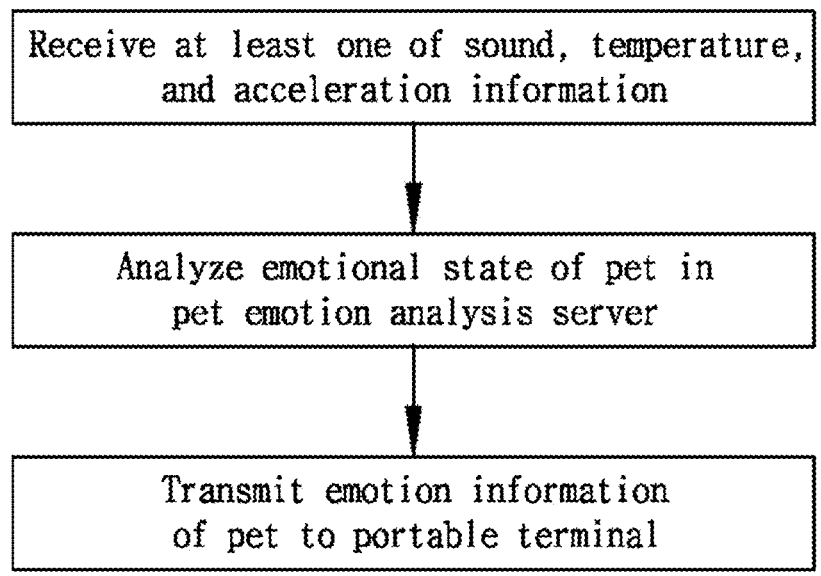
FIG. 2 is a flowchart conceptually illustrating a method for detecting an emotional state of a companion animal in accordance with the present disclosure.

FIG. 2 is a flowchart conceptually illustrating a method for detecting an emotional state of a companion animal in accordance with the present disclosure.

As illustrated in FIG. 2, the method for detecting the emotional state of the companion animal in accordance with the present disclosure includes (1) a step of collecting the sound information, temperature information, acceleration information (activity information) of the companion animal in the state information collecting device through the microphone and sound sensor, temperature sensor, or acceleration sensor; (2) a step of analyzing the emotional state of the companion animal by transmitting the sound information, temperature information, and acceleration information (activity information) to the companion-animal emotion analysis server; and (3) a step of wirelessly transmitting the analyzed emotion information of the companion animal to the portable terminal possessed by the animal owner (or guardian). For reference, the portable terminal is equipped with the predetermined application which may send and receive data to and from the companion-animal emotion analysis server and may output the emotional state information of the companion animal transmitted from the companion-animal emotion analysis server.

Hereinafter, the important technical idea of the method for detecting the emotional state of the companion animal proposed in the present disclosure will be described in detail.

The method for detecting the emotional state of the companion animal in accordance with an embodiment of the present disclosure may include the following steps.

(a) a step of wearing, on a portion of an animal body, the state information collecting device which receives the state information of the companion animal;

(b) a step of selecting and inputting a kind of the companion animal through the input unit of the state information collecting device;

(c) a step of receiving the sound of the companion animal through the microphone that is a component of the state information collecting device, on the basis of a predetermined time;

(d) a step of transmitting the kind information and the sound information of the companion animal to the companion-animal emotion analysis server using a wireless communication network;

(e) a step of extracting characteristic information of the sound information;

(f) a step of selecting predetermined state information corresponding to the kind information and the characteristic information of the companion animal in the database; and (g) a step of transmitting the state information to the portable terminal of the animal guardian using a wireless communication network.

The sound received through the microphone in step (c) is sampled in a predetermined sampling period in a time domain, and then is converted into a digital signal to be transmitted to the companion-animal emotion analysis server in step (d). The state information may include various emotional states (e.g., angry state, surprised state, greeting state, sick state, happy state, etc.) of the companion animal.

Meanwhile, in the present disclosure, the extraction of the characteristic information in step (e) may be performed by extracting the digital information of the sound using spectrogram information for time and frequency domains.

One of the main technical ideas of the present disclosure relates to how to extract the sound feature of the companion animal.

The present disclosure is intended to extract the feature of the companion-animal sound through various experiments.

Figure 3:
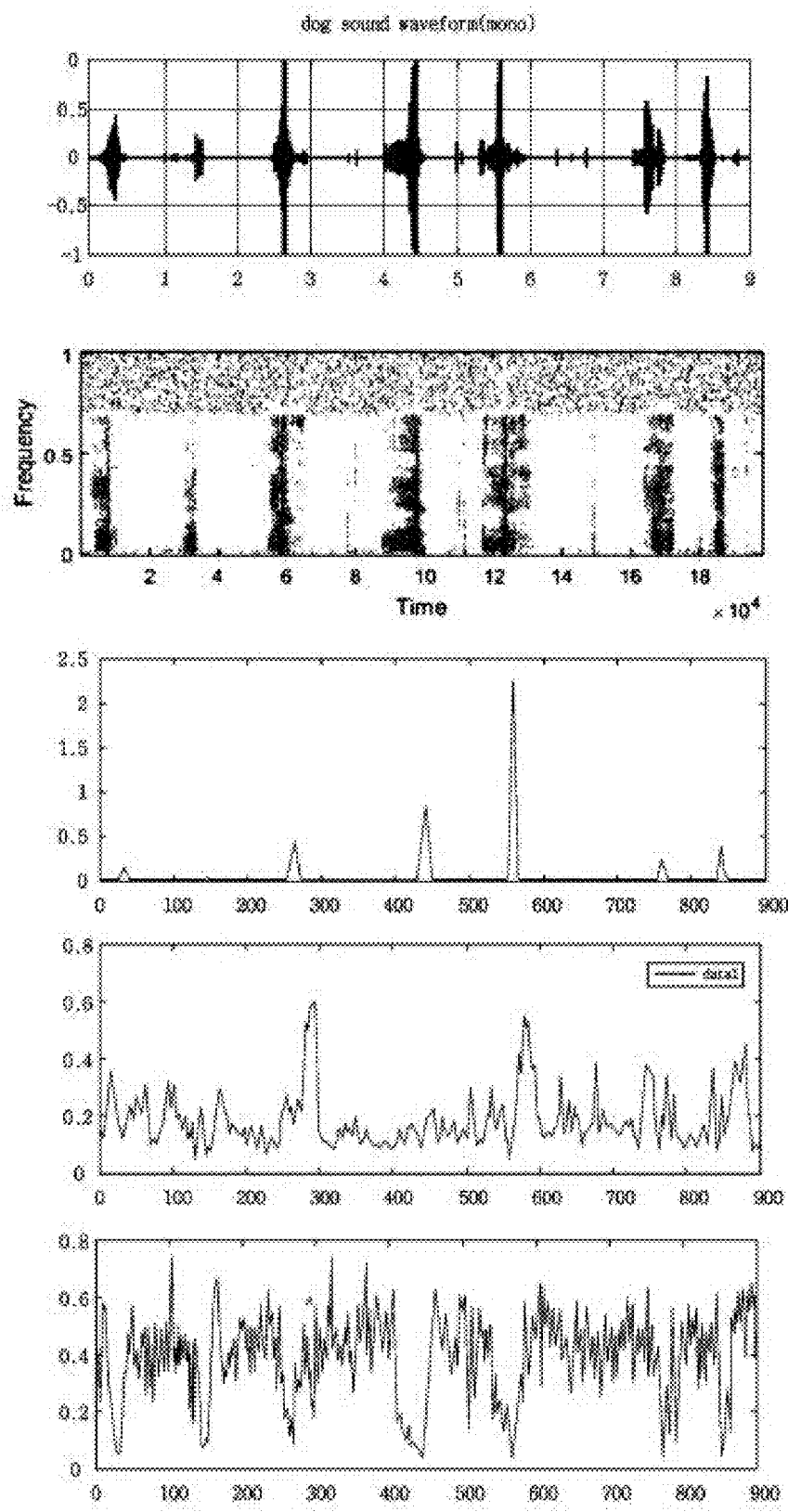
FIG. 3 illustrates an experimental example of a method for detecting an emotional state of a dog as a companion animal.

FIG. 3 illustrates an experimental example of the present disclosure.

In FIG. 3, the feature of the sound of a specific kind of dog which is a kind of pet is shown. As such, in the present disclosure, various features related to time, frequency, short time energy, short time zero crossing, spectrum flatness measure, etc. for the sound of the companion animal are extracted and then made into the database.

These features are extracted through the following method.

[Feature Vector Extraction]

In the feature vector extracting method, it is important to extract an original signal to include key information well according to the purpose of work which is to be performed. Generally, an audio classification deep learning algorithm mainly uses Mel-spectrogram.

However, the dog's barking sound is a noise-like signal made by the combination of various frequency components rather than the presence or absence of specific harmonic components like a musical signal. Therefore, since information about tone is considered as being more important, MFCC (Mel-frequency cepstral coefficient) components are extracted and a comparative experiment is conducted between the Mel-spectrogram for commonly used characteristic vector and a spectrogram for more basic features.

Spectrogram

This is a result of converting a sound signal that is a one-dimensional vector over time into a time-frequency vector through STFT (Short-Time Fourier Transform) to convert the sound signal into a form usable for deep learning. This is the most basic form of time-frequency representation, and represents energy information for each frequency as a vector from 0 to sampling frequency/2 (Hz). Generally, a vertical axis represents frequency information, while a horizontal axis represents time information.

Mel-Spectrogram

The spectrogram is represented in frequency (Hz). Since the spectrogram has too much information to directly classify sound, there is a high possibility that classification algorithm learns unessential characteristics rather than important characteristics. One of methods that abbreviate information while including an entire frequency domain represented by the spectrogram is to make the spectrogram pass through an audio filter bank.

The Mel-spectrogram abbreviates the information of the spectrogram using a mel filter bank having an output similar to that of a human cochlea. A human can separate adjacent frequencies well in a low-frequency band, but a human's ability to distinguish frequencies in a high-frequency band is deteriorated. Based on this fact, the mel filter bank is designed so that a window size increases as a frequency increases.

MFCC (Mel-Frequency Cepstral Coefficient)

The present disclosure further uses MFCC. This converts the Mel-spectrogram into a log-scale, and then takes discrete cosine transform (DCT). In this process, some coefficients having small values are removed. An algorithm code for extracting a vector is based on a python-based open library Librosa which is widely used in audio information analysis research.

Figure 4:
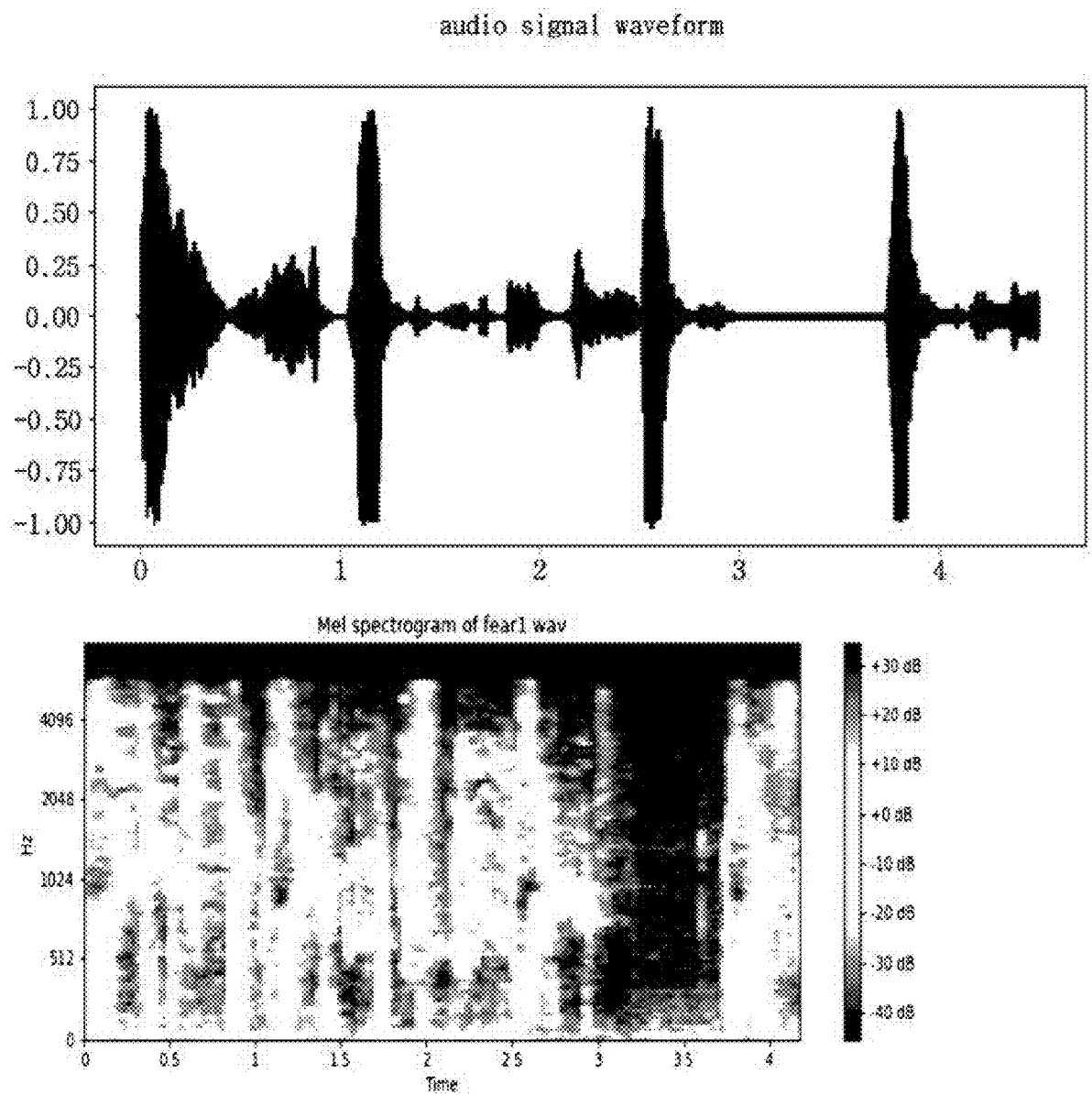
FIG. 4 illustrates an example of the audio signal waveform, Mel-spectrogram, and MFCC characteristic vector of a fear state among pet sounds.
Figure 5:
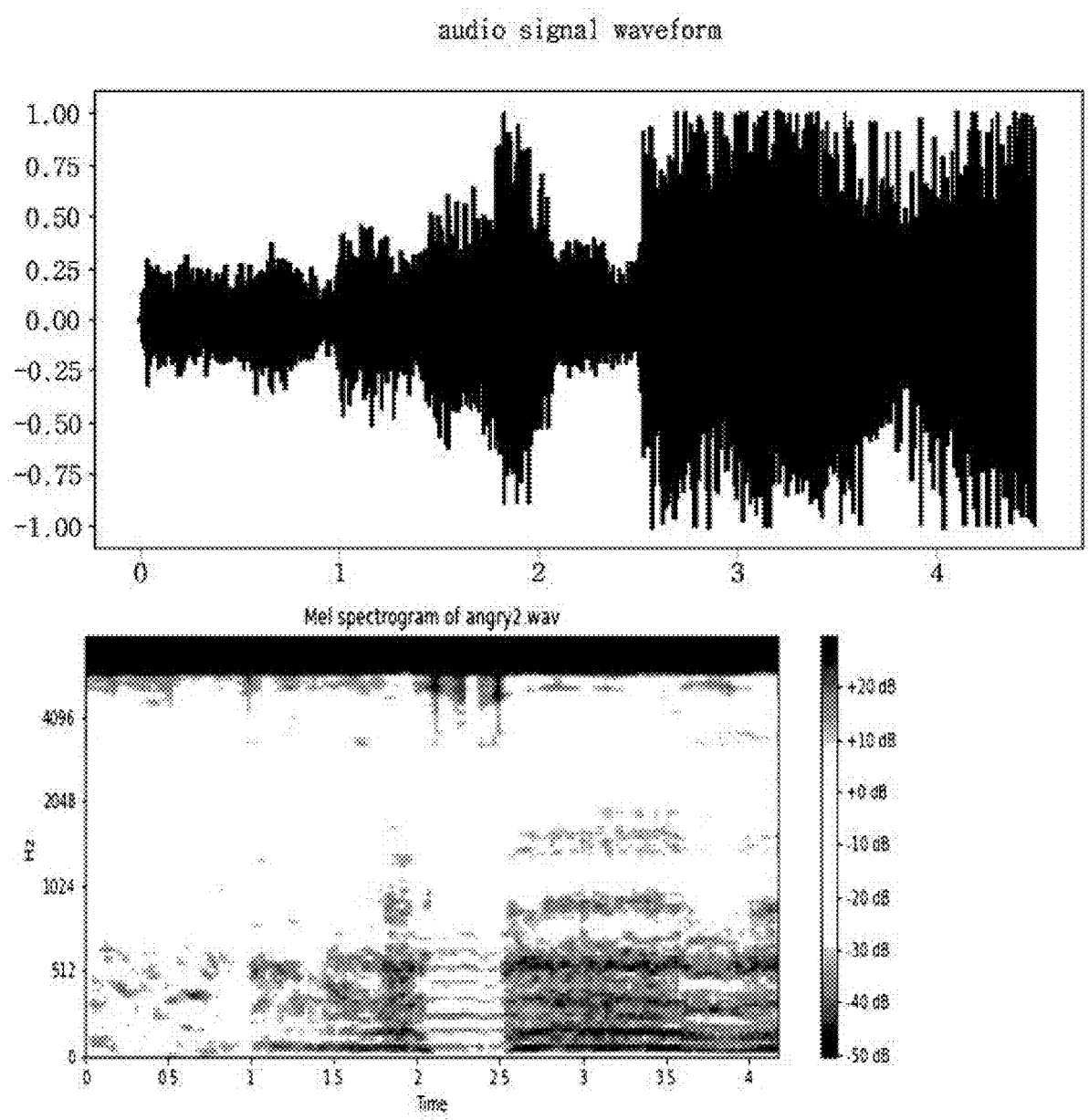
FIG. 5 illustrates an example of the audio signal waveform, Mel-spectrogram, and MFCC characteristic vector of an angry state among pet sounds.
Figure 6:
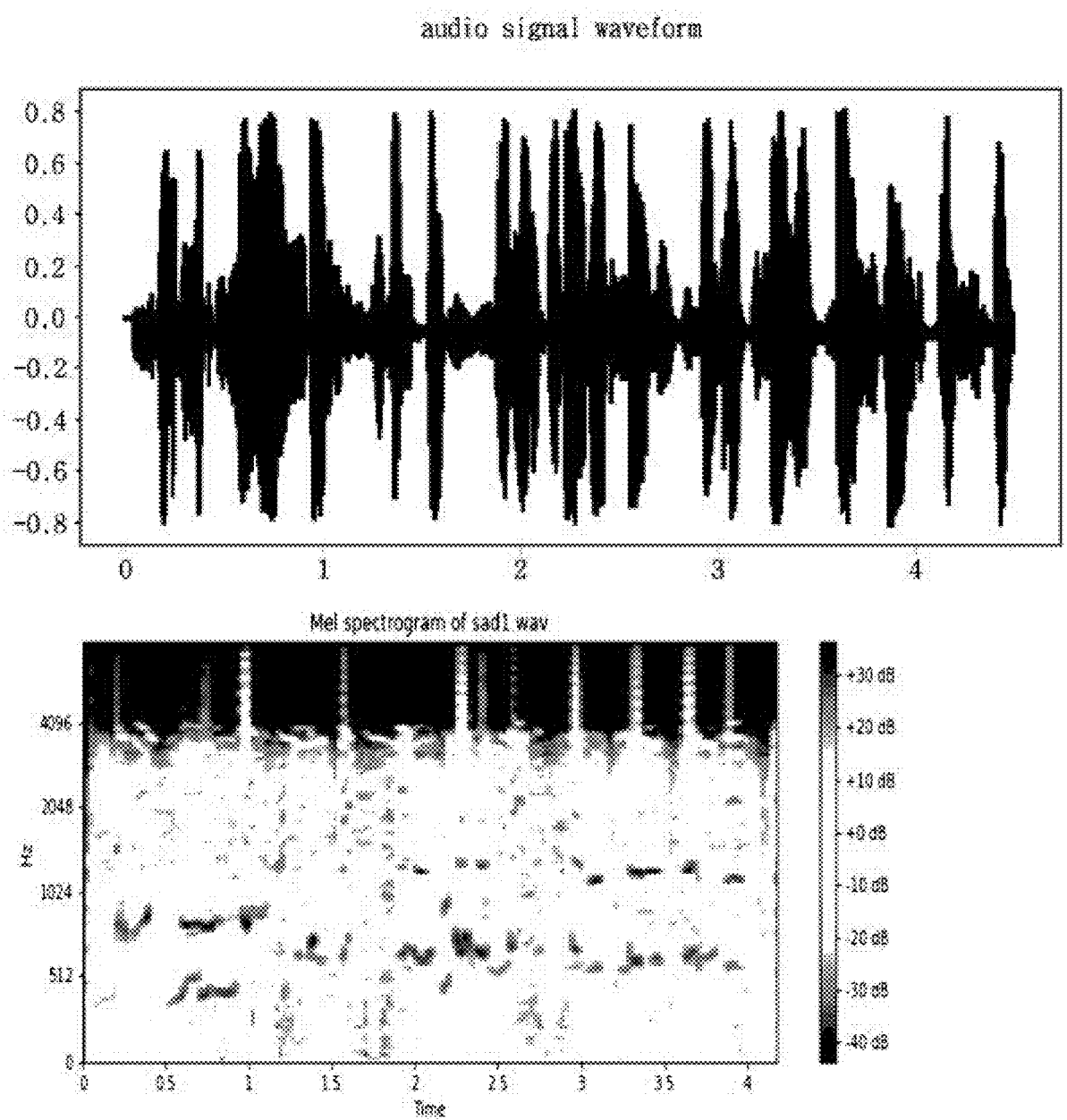
FIG. 6 illustrates an example of the audio signal waveform, Mel-spectrogram, and MFCC characteristic vector of a sad state among pet sounds.
Figure 7:
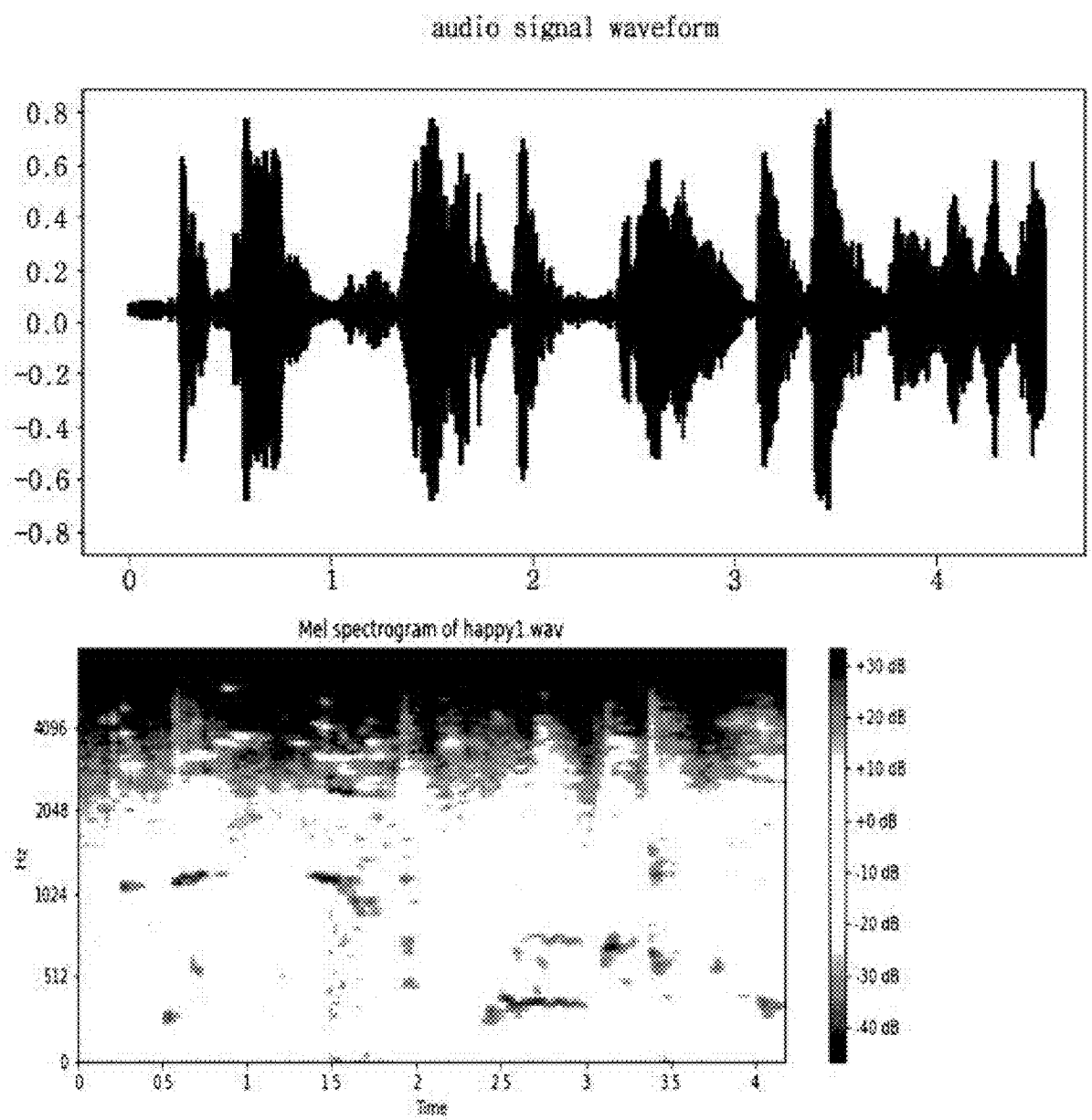
FIG. 7 illustrates an example of the audio signal waveform, Mel-spectrogram, and MFCC characteristic vector of a happy state among pet sounds.

In the present disclosure, FIG. 4 illustrates an example of the audio signal waveform, Mel-spectrogram, and MFCC characteristic vector of a fear state among pet sounds, FIG. 5 illustrates an example of the audio signal waveform, Mel-spectrogram, and MFCC characteristic vector of an angry state, FIG. 6 illustrates an example of the audio signal waveform, Mel-spectrogram, and MFCC characteristic vector of a sad state, and FIG. 7 illustrates an example of the audio signal waveform, Mel-spectrogram, and MFCC characteristic vector of a happy state. This may be organized in various patterns depending on the kind of the companion animal.

In the present disclosure, the experimental results are made into the database. When the sound of the companion animal is input through the microphone and sound sensor, the emotional state of the companion animal may be estimated with a predetermined probability, based on the database.

In addition, regarding the implementation of the present disclosure, the reason why the acceleration sensor is used in the present disclosure is as follows: the case of analyzing the acceleration information of the acceleration sensor (module) attached to the neck or four ankles in addition to analyzing the companion-animal sound may be more precise than the case of analyzing the emotional state of the companion animal only with the sound.

For example, when the companion animal barks with a growl in a tension state, there are many cases where a change in information of the acceleration sensors attached to four ankles is small because the feet are often fixed to the ground. In contrast, when the companion animal is in a good mood, the companion animal often barks with a cheerful sound while lifting the forefoot. In this case, an information value range of the acceleration sensor attached to the forefoot may be completely different from an acceleration information value range of the hind leg coming into the contact with the ground.

The present disclosure is configured to more precisely analyze the emotional state of the companion animal in consideration of both a predetermined sound generated when the companion animal barks and a change in behavior or posture, because a change in movement of the forefoot and the hind leg is different depending on the emotional state of the companion animal, in addition to the sound of the companion animal.

Further, according to the present disclosure, a GPS module may be provided in the state information collecting device to check the position of the companion animal, and the state information collecting device may wirelessly communicate with the acceleration sensor module which may be attached to the external server or ankle through the communication unit of the state information collecting device.

Furthermore, the information about the emotional state of the companion animal may be more precisely analyzed by combining the sound information of the companion animal which is input through the microphone and sound sensor, the activity information which is input through the acceleration sensor, and the temperature information which is input through the temperature sensor, and the abnormal condition of the body may be checked by determining whether the temperature and the activity of the companion animal are normal or abnormal.

Although the present disclosure was described with reference to specific embodiments shown in the drawings, it is apparent to those skilled in the art that the present invention may be changed and modified in various ways without departing from the scope of the present invention, which is described in the following claims.

The present disclosure is applicable to a system for detecting an emotional state of a companion animal, configured to detect sound information and movement information of the companion animal, analyze the emotional state of the companion animal, and transmit analyzed emotional state information to a portable terminal of an animal guardian (owner), thus causing the guardian to recognize the emotional state.

The invention claimed is:

1. A method for detecting an emotional state of a companion animal, the method comprising:
   (a) wearing, on a portion of an animal body, a state information collecting device which receives state information of the companion animal;
   (b) selecting and inputting a kind of the companion animal through an input unit of the state information collecting device;
   (c) receiving a sound of the companion animal through a microphone and sound sensor that is a component of the state information collecting device, on the basis of a predetermined time;
   (d) transmitting kind information and sound information of the companion animal to a companion-animal emotion analysis server using a wireless communication network;
   (e) extracting characteristic information of the sound information;

(f) selecting predetermined state information corresponding to the kind information and the characteristic information of the companion animal in a database; and (g) transmitting the state information to a portable terminal of an animal guardian using a wireless communication network, wherein the sound received through the microphone and sound sensor in (c) is sampled in a predetermined sampling period in a time domain, and then is converted into a digital signal to be transmitted to the companion-animal emotion analysis server in (d), and wherein the state information is any one of various emotional states of the companion animal.

2. The method of claim 1, wherein the extracting of the characteristic information in (e) comprises extracting digital information of the sound using spectrogram information for time and frequency domains.

3. A system for detecting an emotional state of a companion animal, the system comprising:

a state information collecting device comprising a microphone and sound sensor which collects a sound of the companion animal, a temperature sensor which collects a temperature of the companion animal, and an acceleration sensor which collects an activity of the companion animal, the state information collecting device being worn on a body of the companion animal; and a companion-animal emotion analysis server configured to extract characteristic information of sound information of the companion animal transmitted from the state information collecting device, select emotional state information of the companion animal corresponding to the extracted characteristic information from a database, and transmit the selected emotional state information of the companion animal through a wireless communication network to a portable terminal of an animal guardian;

wherein the companion-animal emotion analysis server performs characteristic information extraction of digital information of the sound using spectrogram information for time and frequency domains.

4. The system of claim 3, wherein the sound of the companion animal received through the microphone and sound sensor of the state information collecting device is sampled in a predetermined sampling period in a time domain, and then is converted into a digital signal to be transmitted to the companion-animal emotion analysis server.

5. The system of claim 3, wherein the companion-animal emotion analysis server selects information about the emotional state of the companion animal from the database by combining at least one of temperature information and activity information of the companion animal collected by the temperature sensor and the acceleration sensor of the state information collecting device with the sound information.

* * * * *